US008516751B2

(12) United States Patent
Konduc et al.

(10) Patent No.: US 8,516,751 B2
(45) Date of Patent: Aug. 27, 2013

(54) MOBILE DRILLING RIG

(75) Inventors: Kameron Wayne Konduc, Edmonton (CA); Jonathan Douglas Callaghan, Edmonton (CA); Timothy Scott Anderson, Edmonton (CA)

(73) Assignee: National Oilwell Varco L.P., Houston, TX (US)

( * ) Notice: Subject to any disclaimer, the term of this patent is extended or adjusted under 35 U.S.C. 154(b) by 1041 days.

(21) Appl. No.: 12/152,651

(22) Filed: May 15, 2008

(65) Prior Publication Data
US 2009/0283324 A1 Nov. 19, 2009

(51) Int. Cl.
*B66C 23/34* (2006.01)
*B66C 23/26* (2006.01)
*B66C 23/50* (2006.01)

(52) U.S. Cl.
USPC ................. 52/112; 52/120; 52/123.1; 52/143

(58) Field of Classification Search
USPC ................ 52/112, 115, 116, 120, 123.1, 117; 414/332, 809, 919; 173/184, 185, 28
See application file for complete search history.

(56) References Cited

U.S. PATENT DOCUMENTS

| | | | | |
|---|---|---|---|---|
| 3,109,523 A * | 11/1963 | Moller | ............. | 52/115 |
| 3,334,849 A | 8/1967 | Bronder | ............. | 248/13 |
| 3,340,938 A | 9/1967 | Wilson | | |
| 3,365,008 A * | 1/1968 | Zimmerman et al. | ......... | 175/85 |
| 3,807,109 A | 4/1974 | Jenkins et al. | ............. | 52/120 |
| 4,021,978 A | 5/1977 | Busse et al. | ............. | 52/118 |
| 4,231,200 A * | 11/1980 | Henderson | ............. | 52/111 |
| 4,290,495 A | 9/1981 | Elliston | ............. | 175/85 |
| 4,368,602 A | 1/1983 | Manten | ............. | 52/115 |
| 4,371,046 A | 2/1983 | Reed | ............. | 175/57 |
| 4,375,892 A | 3/1983 | Jenkins et al. | ............. | 280/43.23 |
| 4,489,526 A | 12/1984 | Cummins | ............. | 52/125.6 |
| 4,491,449 A * | 1/1985 | Hawkins | ............. | 414/10 |
| 4,569,168 A | 2/1986 | McGovney et al. | ............. | 52/122.1 |
| 4,591,006 A | 5/1986 | Hutchison et al. | ............. | 175/52 |
| 4,630,425 A | 12/1986 | Reed | ............. | 52/745 |
| 4,684,314 A | 8/1987 | Luth | ............. | 414/745 |
| 4,757,592 A * | 7/1988 | Reed | ............. | 29/429 |
| 5,109,934 A | 5/1992 | Mochizuki | ............. | 175/170 |
| 5,251,709 A | 10/1993 | Richardson | ............. | 175/220 |
| 5,524,398 A * | 6/1996 | Miller et al. | ............. | 52/121 |
| 6,301,841 B1 * | 10/2001 | Rhebergen et al. | ............. | 52/123.1 |

(Continued)

FOREIGN PATENT DOCUMENTS
EP 379335 A1 * 7/1990

OTHER PUBLICATIONS

PCT/GB2009/050524 International Search Report (Jan. 26, 2010).
Mobile Rigs, National Oilwell, 8 pp., 2005.
Rig System, National Oilwell, 8 pp. 2004.

*Primary Examiner* — Phi A
(74) *Attorney, Agent, or Firm* — Williams, Morgan & Amerson, P.C.

(57) ABSTRACT

Mobile drilling rigs and methods for moving drilling rigs are disclosed which, in one aspect, include wheel assemblies connected to a rig which wheel assemblies are selectively movable from a rig drilling position to a rig movement position. This abstract is provided to comply with the rules requiring an abstract which will allow a searcher or other reader to quickly ascertain the subject matter of the technical disclosure and is submitted with the understanding that it will not be used to interpret or limit the scope or meaning of the claims, 37 C.F.R. 1.72(b).

43 Claims, 12 Drawing Sheets

(56) References Cited

U.S. PATENT DOCUMENTS

| | | | |
|---|---|---|---|
| 6,474,926 B2 | 11/2002 | Weiss | 414/332 |
| 6,594,960 B2* | 7/2003 | Brittain et al. | 52/117 |
| 6,598,702 B1* | 7/2003 | McGillewie et al. | 182/2.6 |
| 6,634,436 B1 | 10/2003 | Desai | 173/1 |
| 6,782,667 B2* | 8/2004 | Henderson | 52/116 |
| 6,848,515 B2 | 2/2005 | Orr et al. | 173/1 |
| 6,860,337 B1 | 3/2005 | Orr et al. | 173/28 |
| 7,308,953 B2 | 12/2007 | Barnes | 175/203 |
| 7,357,616 B2 | 4/2008 | Andrews et al. | 414/332 |
| 2004/0240973 A1 | 12/2004 | Andrews et al. | 414/332 |
| 2005/0236790 A1 | 10/2005 | Carter | 280/79.11 |
| 2006/0213653 A1 | 9/2006 | Cunningham et al. | 166/77.1 |

* cited by examiner

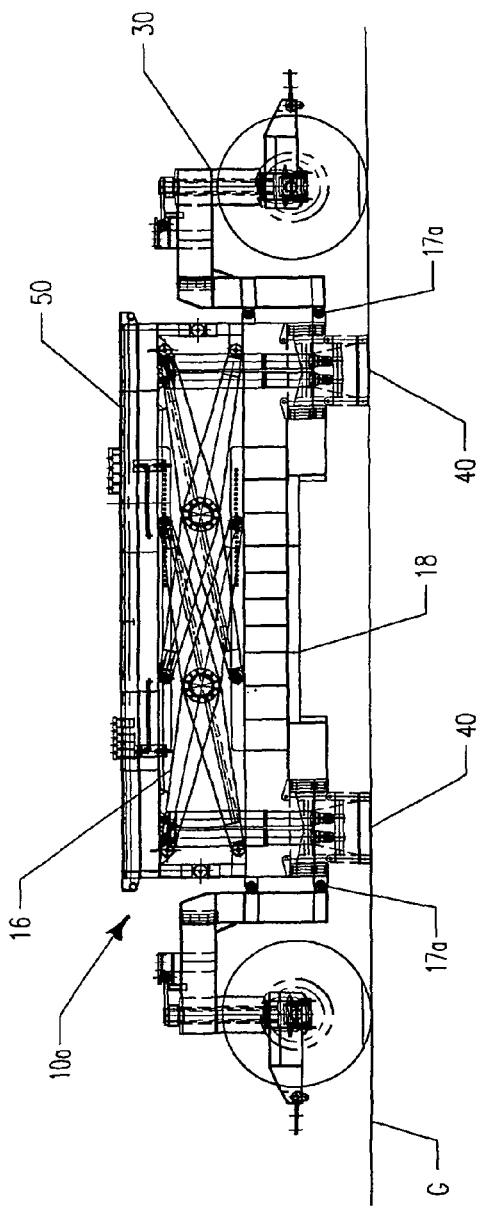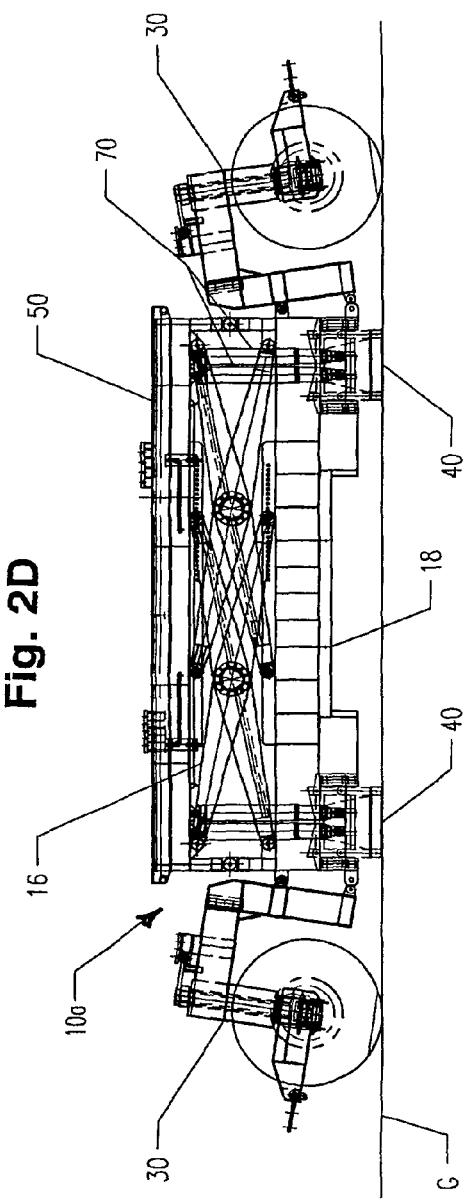

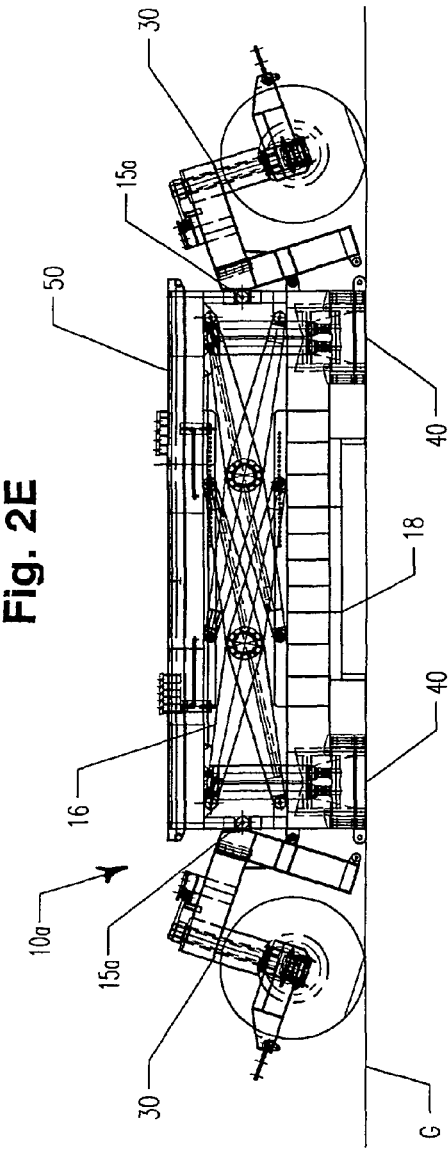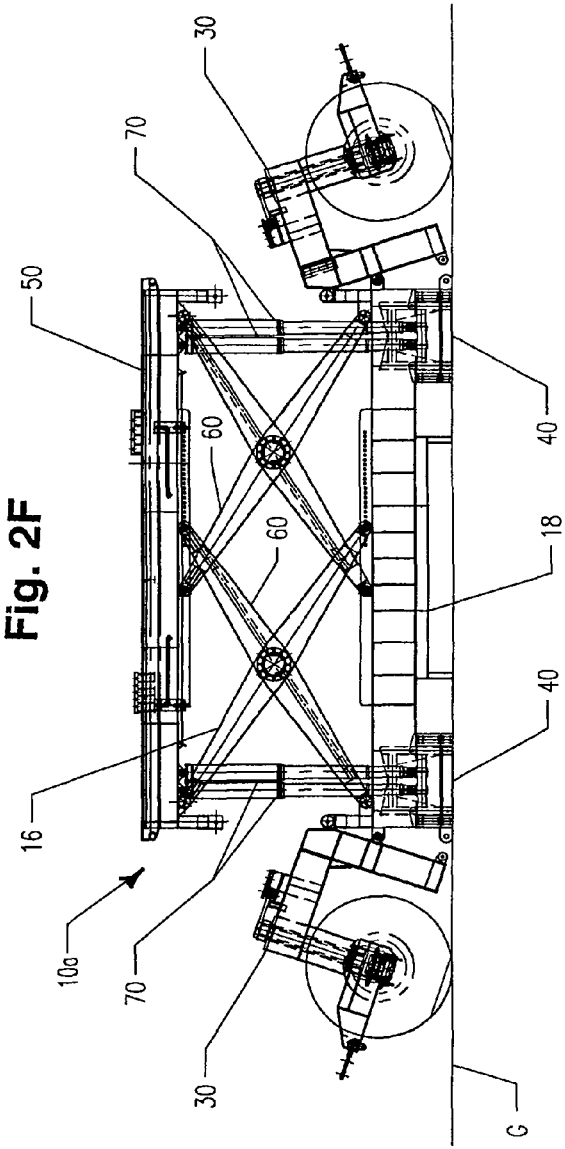

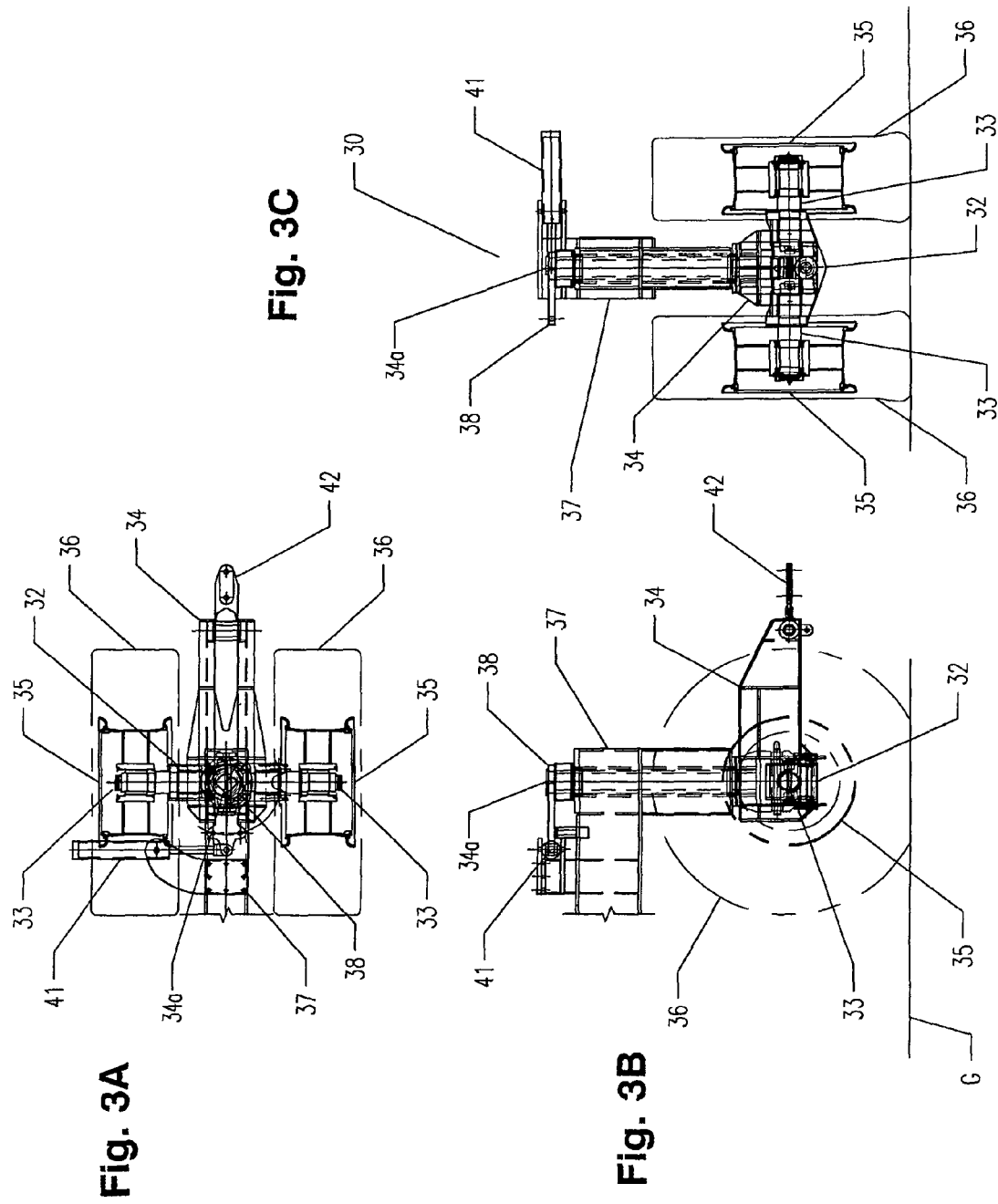

MOBILE DRILLING RIG

BACKGROUND OF THE INVENTION

1. Field of the Invention

This invention is directed to drilling rigs with erectable masts and substructures; in certain particular aspects, to such rigs that are mobile; and methods for moving a drilling rig.

2. Description of Related Art

The prior art discloses a variety of rigs used in drilling and various wellbore operations, including rigs that are mobile; for example, and not by way of limitation, U.S. Pat. Nos. 3,340,938; 3,807,109; 3,922,825; 3,942,593; 4,269,395; 4,290,495; 4,368,602; 4,489,526; 4,569,168; 4,837,992; 6,634,436; 6,523,319 and the references cited in these patents—all these patents incorporated fully herein for all purposes.

In many land drilling operations, land rigs are delivered to a site, assembled and then disassembled; including, in many cases, raising a rig mast to a vertical operational position. Often as an oilfield becomes mature, wells are drilled deeper into the earth to obtain production. Oil rigs are getting progressively larger to meet these needs. In the past, a 1500 hp rig was sufficient to handle most drilling. These rigs more recently have been supplanted by larger 2000 hp rigs. Currently, 3000 hp rigs are being made, but are not yet widely used. A 3000 hp rig typically has a 36 to 37 foot high drillfloor, a 156 foot clear height mast, a 1,500,000 pound hookload, a 1,300,000 pound rotary load, and a 1,000,000 pound setback load. Often large drilling rigs, e.g. in the Middle East, are transported between well sites by dismantling the rig into pieces that can be trucked between two well sites which can produce many time-consuming truckloads of rig components resulting in up to four additional weeks of rig downtime (the larger the capacity of the rig, the heavier the loads, and the number of loads also increases); and mounting the drilling module complete with mast on tires. One drawback of a tire-mounted drilling module is tire load capacity and overall rig height. Often, the largest tires that are used are 40×57 earthmover tires.

With certain current rig designs, the largest rigs that can be easily moved are 2000 hp rigs of a box style substructure. This style of design is conducive to even tire loading. A typical 3000 hp rig that has an evenly loaded box style substructure will be too tall to move with a 156 foot mast and a 37 foot drillfloor to get under the power line height restriction with current moving systems (e.g. in countries such as Kuwait where a typical maximum clearance for power lines is 161 feet from the ground to the top of the rig being transported). Anything taller than this will produce the potential for electrical arcing between the mast and the power lines if the rig is being towed on its tires.

Another common style of substructure is the slingshot substructure which is often used in large hookload application. The substructure folds down in order to easily access the drillfloor from the ground level, which aids in rig assembly. Often a substructure of this size is broken down into truck sized loads. Placing a wheeled moving system on certain rigs of this style may not be practical because it is not feasible to easily balance the wheel loads.

U.S. Pat. No. 3,922,825 discloses a rig with a stationary substructure base and a movable substructure base mounted thereon which is coupled to the stationary base and swings upright into an elevated position on a series of struts that are connected to the stationary base with swivel connections at each end. The movable base is otherwise stationary since neither the stationary base nor the movable base are mobile or repositionable without the use of an auxiliary crane or the like. The movable substructure base and the drill mast are raised with a winch mounted on an auxiliary winch truck.

U.S. Pat. No. 3,942,593 discloses a mobile well drilling rig apparatus which has a trailerable telescoping mast and a separate sectionable substructure assembly with a rig base, a working floor, and a rail structure. The mast is conveyed to the top of the substructure by rollers and is raised by hydraulic raising apparatus to an upright position. With such a system the the mast assembly can be relatively long when transporting it and the mast can be unstable during raising. This system uses drawlines and winch apparatus to raise the mast onto the working floor.

U.S. Pat. No. 6,523,319 discloses a drilling rig base and a lower mast section that are collapsible into a compact transportable position. The base is expandable in the field to support a drilling platform and equipment, and the telescoping mast is also expandable for supporting the crown block and cables of the drawworks. The rig may have a plurality of beams, the outer beams being collapsible to a transportable position for placing on a single truck or trailer, and the A-frame lower mast section which is collapsible to a transportable position for placing on a single truck or trailer. In one aspect, a mobile, collapsible drilling rig base and drilling platform are disclosed which haves: a base having a plurality of parallel beams; the beams being in a horizontal plane and including inner beams and outer beams: the outer beams being collapsible in said horizontal plane to a transportable position; and a drilling platform attached to the base that is elevatable above the base.

U.S. Pat. No. 6,634,436 discloses a mobile land drilling apparatus and method. The rig has a mobile telescoping substructure box. A lifting apparatus selectively supports the mobile telescoping substructure box unit in a raised position and lowered position. An extension cylinder further extends the mobile telescoping substructure box unit in telescopic extension. A stationary frame member and a telescoping frame member have a plurality of cables attached thereto for supporting the telescoping frame member when extended. A trolley winch allows completion of the rig assembly without an external crane.

U.S. Pat. No. 7,357,616 discloses oil rig capable of being at least partially disassembled to form at least two portions, such as a top half and bottom half, and an associated structure for transport. An oil rig top portion may be loaded onto a trailer for transport separate from a bottom portion. The trailer includes a bottom frame, a top frame, a structure operably associated with said bottom and top frames for moving the top and bottom frames away from and towards one another, and a moving means attached to the at least bottom frame to allow the trailer to be moved along the support surface. The trailer may be towed by a truck or other vehicle. In one aspect a method is disclosed for transporting an oil rig, including: disassembling the oil rig to form a top portion with a rig floor and a mast and bottom portion with a substructure; transporting the top portion separately from the bottom portion; transporting the rig floor on a trailer; raising a top surface of the trailer to accept the rig floor; and prior to the step of transporting the rig floor on the trailer, lowering the top surface of the trailer. In one aspect, a trailer is disclosed for moving a part of an oil rig along a support surface, the trailer having: a bottom frame; a top frame; a structure operably associated with the bottom and top frames for moving the top and bottom frames away from and towards one another and further operative to temporarily fix the position of the top and bottom frames with respect to one another, the structure having at least one hydraulic piston; an alignment mechanism affixed to one of the top and bottom frame, the alignment mechanism operative to align the top frame with a top surface of the oil rig; an I-beam affixed to the top surface and operative to facilitate loading the part of the oil rig onto the trailer; and a moving means attached to at least the bottom frame to allow the trailer to be moved along the support surface.

BRIEF SUMMARY OF THE INVENTION

The present invention, in certain aspects, discloses a mobile drilling rig with integral wheel assemblies selectively changeable from a drilling mode position to a moving mode position. In the moving mode position, the mobile drilling rig is movable on the wheel assemblies from one location to another.

In certain aspects, the present invention discloses a system that includes a land rig with an erectable substructure; an erectable mast; and movement apparatus on which the substructure is mounted for moving the rig from one location to another. In one aspect, the present invention discloses a mobile drilling rig with a base box, a plurality of wheel assemblies pivotably connected to the base box, each of the plurality of wheel assemblies selectively pivotable from a first position to a second position, the first position for moving the mobile drilling rig from a first location to a second location.

Accordingly, the present invention includes features and advantages which are believed to enable it to advance rig movement technology. Characteristics and advantages of the present invention described above and additional features and benefits will be readily apparent to those skilled in the art upon consideration of the following detailed description of preferred embodiments and referring to the accompanying drawings.

Certain embodiments of this invention are not limited to any particular individual feature disclosed here, but include combinations of them distinguished from the prior art in their structures, functions, and/or results achieved. Features of the invention have been broadly described so that the detailed descriptions that follow may be better understood, and in order that the contributions of this invention to the arts may be better appreciated. There are, of course, additional aspects of the invention described below and which may be included in the subject matter of the claims to this invention. Those skilled in the art who have the benefit of this invention, its teachings, and suggestions will appreciate that the conceptions of this disclosure may be used as a creative basis for designing other structures, methods and systems for carrying out and practicing the present invention. The claims of this invention are to be read to include any legally equivalent devices or methods which do not depart from the spirit and scope of the present invention.

What follows are some of, but not all, the objects of this invention. In addition to the specific objects stated below for at least certain preferred embodiments of the invention, there are other objects and purposes which will be readily apparent to one of skill in this art who has the benefit of this invention's teachings and disclosures. It is, therefore, an object of at least certain preferred embodiments of the present invention to provide the embodiments and aspects listed above and:

New, useful, unique, efficient, non-obvious drilling rigs, systems for moving them, and methods for moving them; and Such systems in which a drilling rig has a plurality of wheel assemblies selectively movable into a moving mode to move the drilling rig from one location to another.

The present invention recognizes and addresses the problems and needs in this area and provides a solution to those problems and a satisfactory meeting of those needs in its various possible embodiments and equivalents thereof. To one of skill in this art who has the benefits of this invention's realizations, teachings, disclosures, and suggestions, other purposes and advantages will be appreciated from the following description of certain preferred embodiments, given for the purpose of disclosure, when taken in conjunction with the accompanying drawings. The detail in these descriptions is not intended to thwart this patent's object to claim this invention no matter how others may later attempt to disguise it by variations in form, changes, or additions of further improvements.

The Abstract that is part hereof is to enable the U.S. Patent and Trademark Office and the public generally, and scientists, engineers, researchers, and practitioners in the art who are not familiar with patent terms or legal terms of phraseology to determine quickly from a cursory inspection or review the nature and general area of the disclosure of this invention. The Abstract is neither intended to define the invention, which is done by the claims, nor is it intended to be limiting of the scope of the invention in any way.

It will be understood that the various embodiments of the present invention may include one, some, or all of the disclosed, described, and/or enumerated improvements and/or technical advantages and/or elements in claims to this invention.

Certain aspects, certain embodiments, and certain preferable features of the invention are set out herein. Any combination of aspects or features shown in any aspect or embodiment can be used except where such aspects or features are mutually exclusive.

BRIEF DESCRIPTION OF THE SEVERAL VIEWS OF THE DRAWINGS

A more particular description of embodiments of the invention briefly summarized above may be had by references to the embodiments which are shown in the drawings which form a part of this specification. These drawings illustrate certain preferred embodiments and are not to be used to improperly limit the scope of the invention which may have other equally effective or equivalent embodiments.

FIG. 2C is a side front view of the drilling rig of FIG. 1A showing a step after the step shown in FIG. 2B.

FIG. 2D is a side view of the drilling rig of FIG. 1A showing a step after the step shown in FIG. 2C.

FIG. 2E is a side view of the drilling rig of FIG. 1A showing a step after the step shown in FIG. 2D.

FIG. 2F is a side view of the drilling rig of FIG. 1A showing a step after the step shown in FIG. 2E.

FIG. 3A is a top view of a wheel assembly of the drilling rig of FIG. 1A.

FIG. 3B is a side view of the wheel assembly of FIG. 3A.

FIG. 3C is a front view of the wheel assembly of FIG. 3A.

Figure 1A:
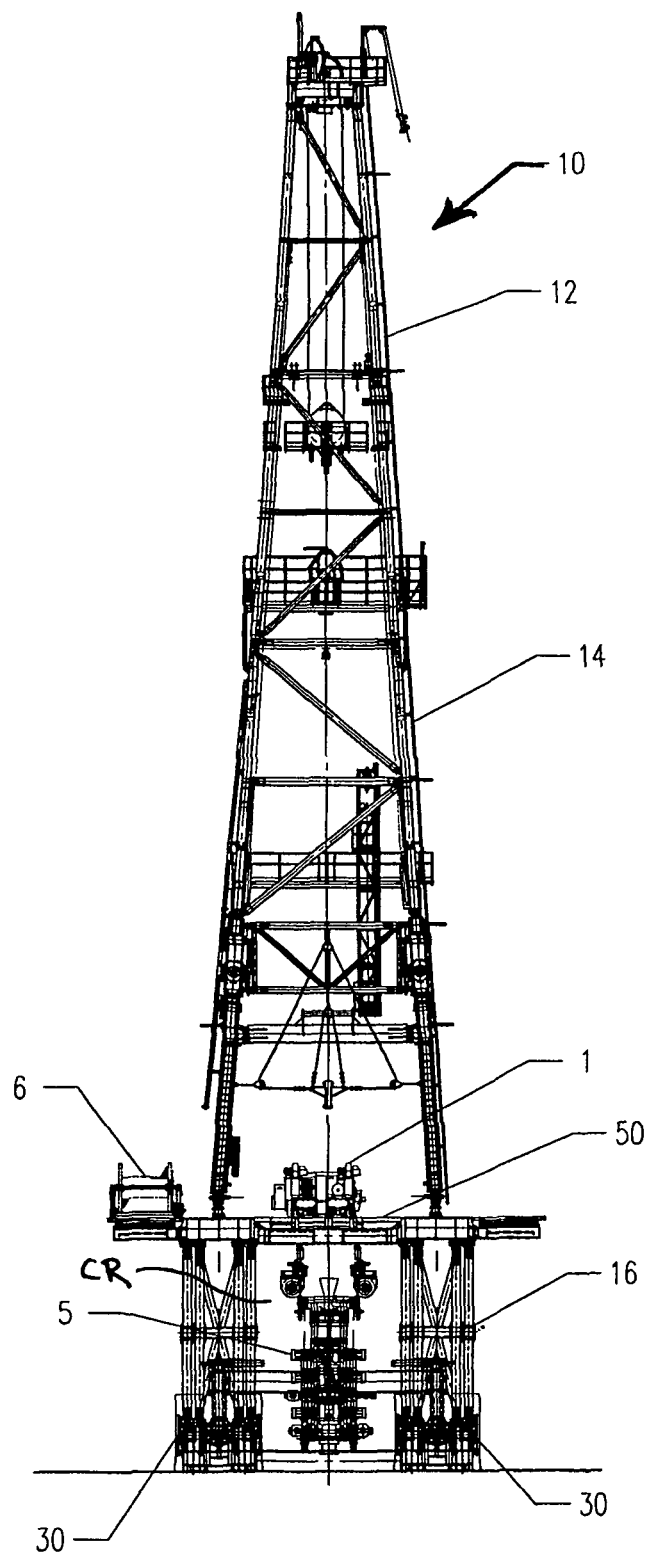
FIG. 1A is an end view of a drilling rig according to the present invention.

Presently preferred embodiments of the invention are shown in the above-identified figures and described in detail below. Various aspects and features of embodiments of the invention are described below and some are set out in the dependent claims. Any combination of aspects and/or features described below or shown in the dependent claims can be used except where such aspects and/or features are mutually exclusive. It should be understood that the appended drawings and description herein are of preferred embodiments and are not intended to limit the invention or the appended claims. On the contrary, the intention is to cover all modifications, equivalents and alternatives falling within the spirit and scope of the invention as defined by the appended claims. In showing and describing the preferred embodiments, like or identical reference numerals are used to identify common or similar elements. The figures are not necessarily to scale and certain features and certain views of the figures may be shown exaggerated in scale or in schematic in the interest of clarity and conciseness.

As used herein and throughout all the various portions (and headings) of this patent, the terms "invention", "present invention" and variations thereof mean one or more embodiment, and are not intended to mean the claimed invention of any particular appended claim(s) or all of the appended claims. Accordingly, the subject or topic of each such reference is not automatically or necessarily part of, or required by, any particular claim(s) merely because of such reference. So long as they are not mutually exclusive or contradictory any aspect or feature or combination of aspects or features of any embodiment disclosed herein may be used in any other embodiment disclosed herein.

DETAILED DESCRIPTION OF THE INVENTION

The present invention provides mobile drilling rigs, systems and methods for rig erection; and systems and methods for moving a drilling rig. This invention's teachings are applicable, inter alia, to any rig which has an erectable substructure.

Figure 1B:
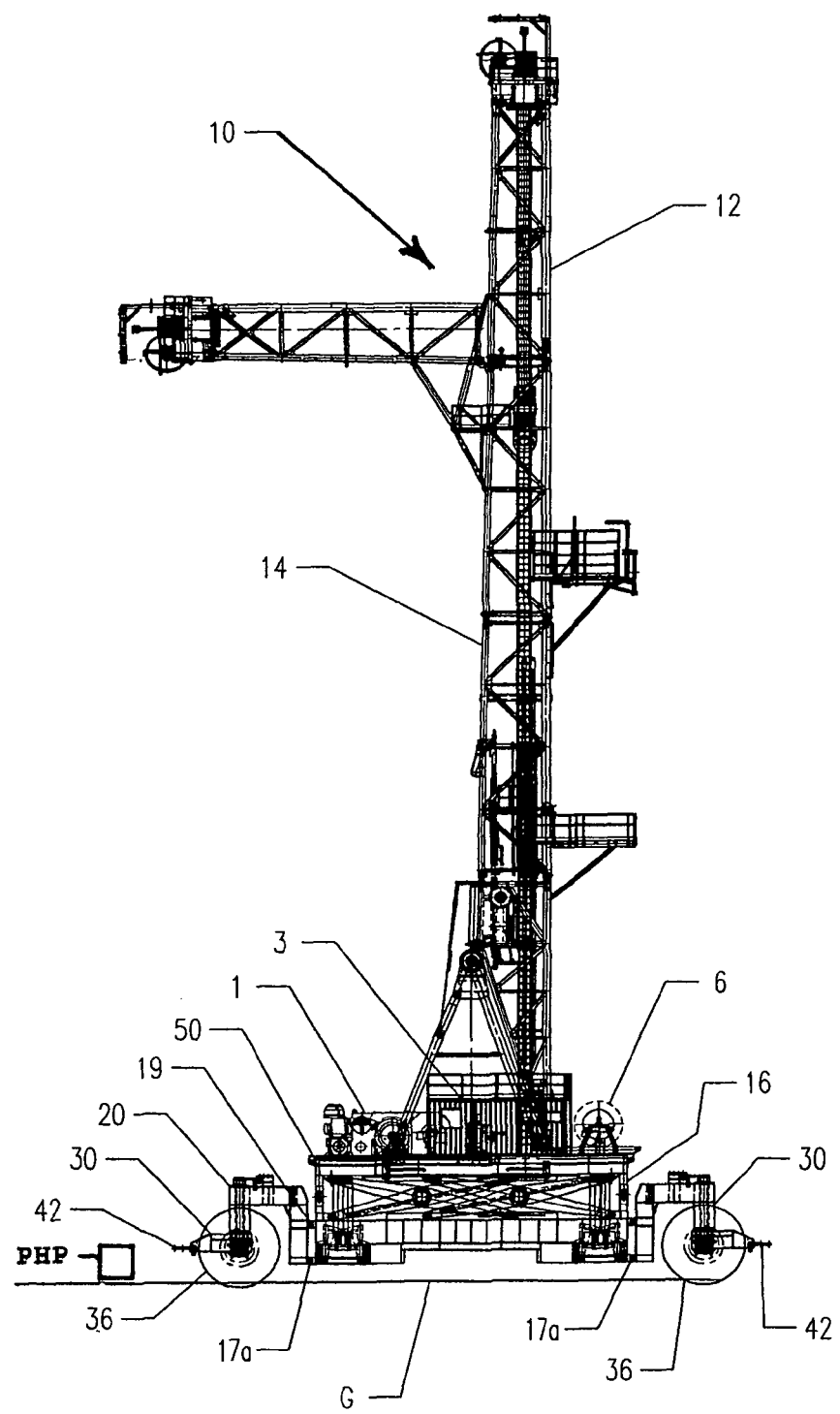
FIG. 1B is a side view of the drilling rig of FIG. 1A.
Figure 1C:
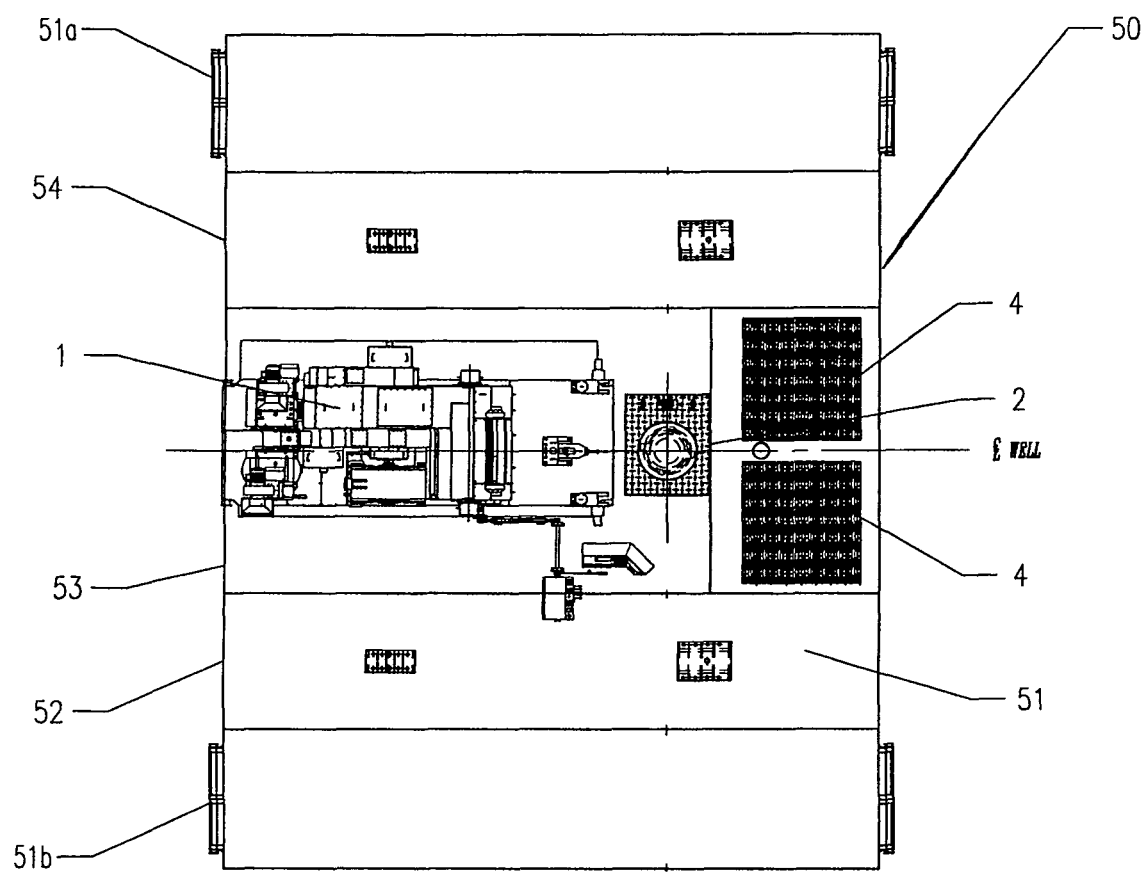
FIG. 1C is a top plan view of a rig floor of the drilling rig of FIG. 1A.
Figure 1D:
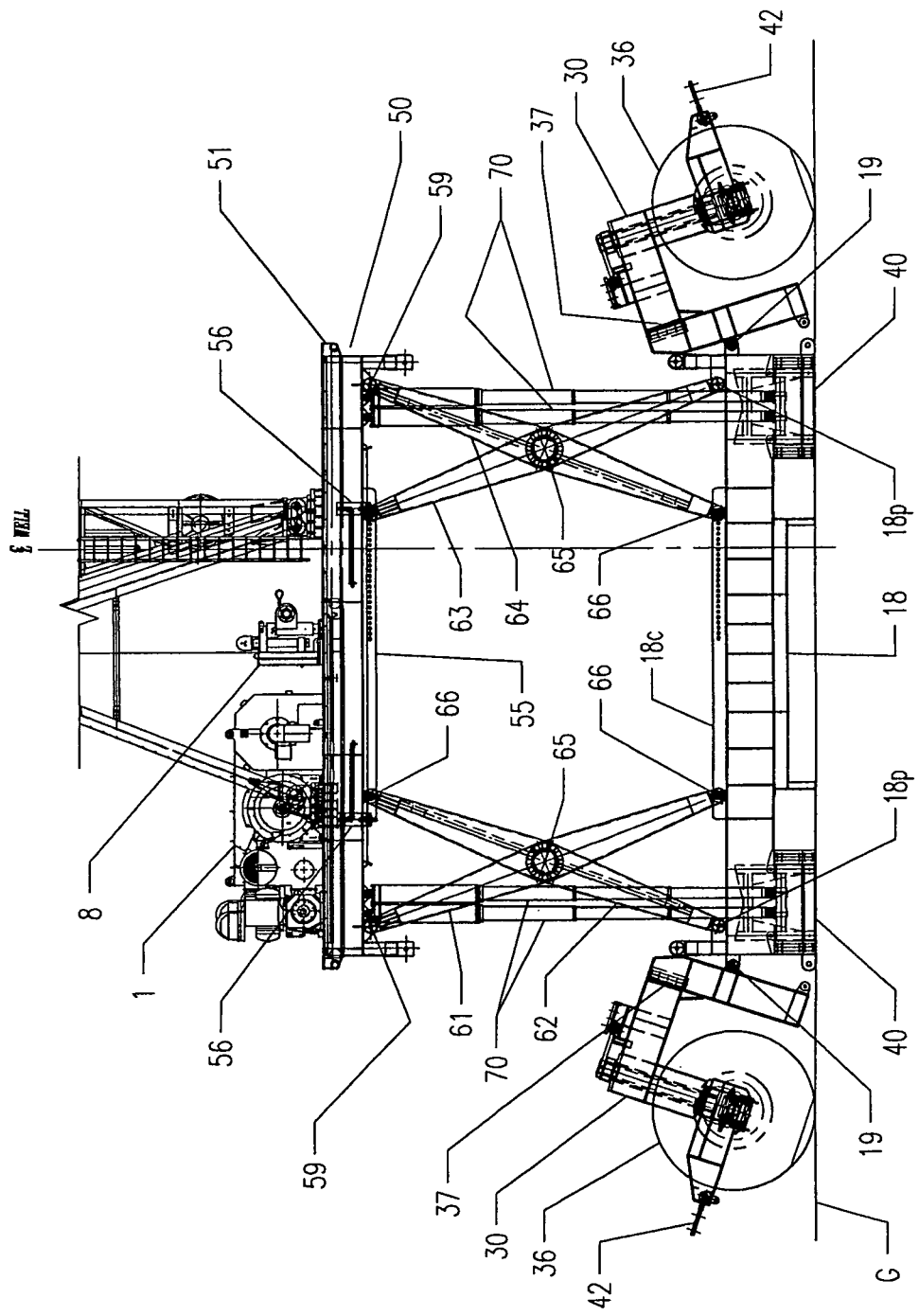
FIG. 1D is a side view of part of the drilling rig of FIG. 1A.
Figure 1E:
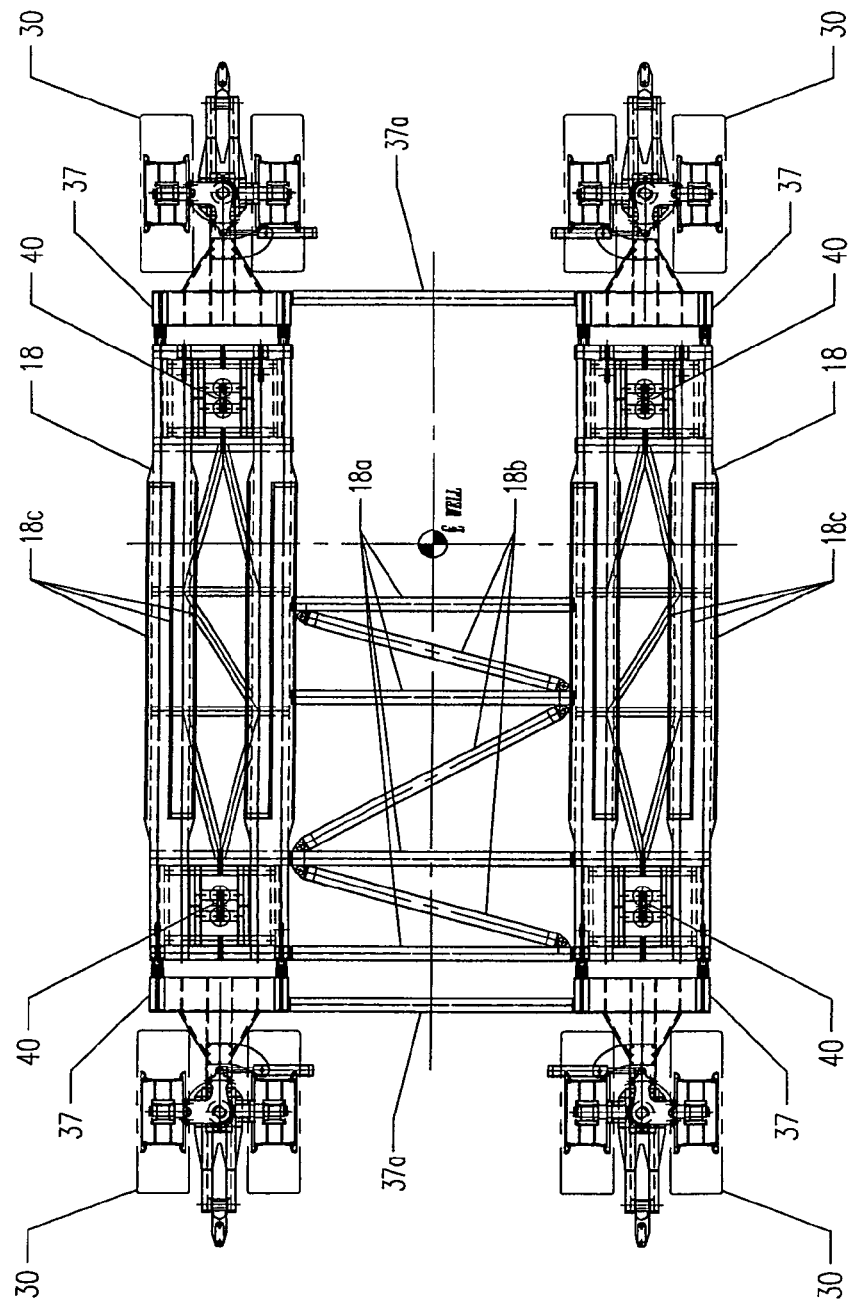
FIG. 1E is a top plan view of wheel assemblies and interconnecting structure of the drilling rig of FIG. 1A.
Figure 1F:
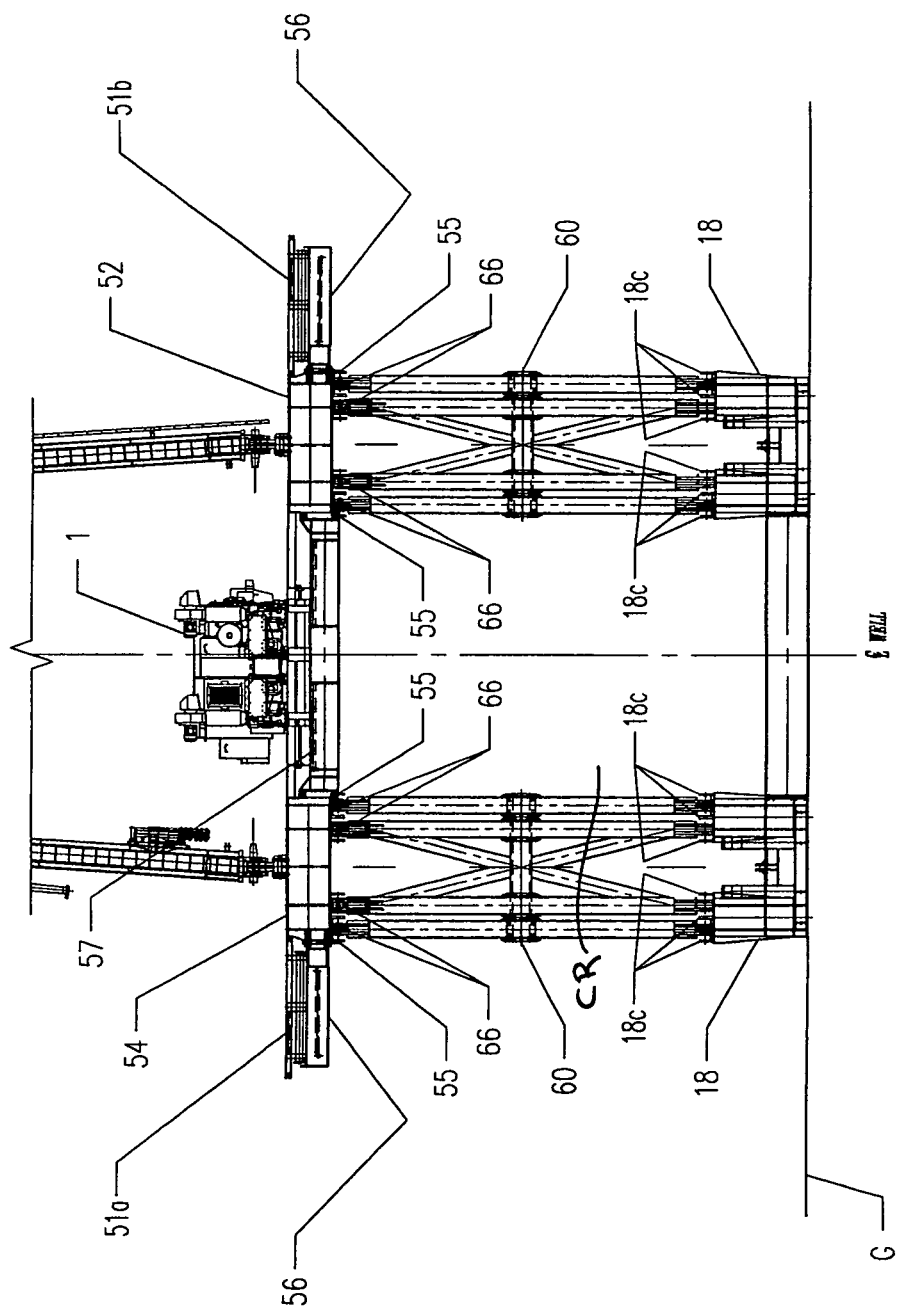
FIG. 1F is an end view showing the drilling floor of FIG. 1C in a raised position.

FIGS. 1A and 1B show a system 10 according to the present invention which includes a drilling rig 12 with a mast 14, a substructure 16, and movement apparatus 20 supporting the substructure 16, the mast 14, and related equipment and structure. The mast 14 may be, as shown, a tilt top mast, or it may be any suitable known mast. The substructure 16 is erectable from a lowered position as shown in FIG. 1B to a raised position as shown in FIGS. 1A and 1D. The system 10 includes typical rig equipment and, apparatuses, e.g., but not limited to, a drawworks 1, a rotary table 2 (see FIG. 1C), a driller cabin/doghouse 3, a setback floor 4, a BOP stack 5, a drill line spooler 6, and hydraulic catheads 8.

The movement apparatuses 20 (see, FIGS. 2G, 3A-3C) include four wheel assemblies 30 which are pivotably mounted to a base box 18 at pivot points 19. Each wheel assembly 30 has two wheels 35 each with a tire 36 and has a lug 31 selectively secured with a removable pin 17a to a lug 17 projecting from the base box 18. Stop members 15 abut top beams 32 of the wheel assemblies 30 when the wheel assemblies 30 pivot at the pivot points 19 to prevent further movement of the top beams 32 toward the substructure 16.

Axles 33 which rotate in trunnions 32 of the wheel assemblies 30 have wheels 35 secured thereto. Each wheel 35 has a tire 36 (e.g., but not limited to 40×57, 76 ply tires). Optionally there is only one wheel for each wheel assembly each with one tire thereon at each of the four corners of a rig. A trunnion support 34 of each wheel assembly is rotatably secured at a wheel pivot 34a to a trunnion load beam 37 which is secured to the base box 18.

The movement apparatuses 20 (see, FIGS. 2G, 3A-3C) include four wheel assemblies 30 which are pivotably mounted to a base box 18 at pivot points 19. Each wheel assembly 30 has two wheels 35 each with a tire 36 and has a lug 31 selectively secured with a removable pin 17a to a lug 17 projecting from the base box 18. Stop members 15 abut top beams 37 of the wheel assemblies 30 when the wheel assemblies 30 pivot at the pivot points 19 to prevent further movement of the top beams 37 toward the substructure 16.

The base box 18 includes base box spreaders 18a (beams that interconnect boxes on each side of the rig) and roller tracks 18c for scissors rollers (described below). Frame connection braces 18b are secured between pairs of base box spreaders 18a. Removable trunnion beam spreaders 37a are connected between pairs of trunnion load beams 37.

Four bearing pad apparatuses 40 are secured to the base box 18 in a raised position by pins 40a. When the rig 12 is in a drilling mode (e.g. see FIGS. 1A and 2G), the bearing pads 40 rest on the ground G. The bearing pads 40 have a limited travel length (e.g., see FIGS. 2B, 2C). The bearing pads 40 are movable by cylinder apparatuses 70 (described below).

The substructure 16 supports a drillfloor 50 which includes a drillfloor skid 51 with ends 51a and 51b supported by drill floor skid supports 56; a driller's side floor box 52; a central drill floor 53; and an off driller's side floor box 54. The drillfloor boxes 52, 54 include roller tracks 55 for scissors rollers (described below). Drawworks support spreaders 57 extend between the drill floor boxes 52, 54.

The substructure 16 has four scissors apparatuses 60, two front and two rear. Each front scissors apparatus has a two outer scissors 61 and two inner scissors 62. Each rear scissors has two outer scissors 63 and two inner scissors 64. The front and rear scissors parts are secured together with center pipe connections 65. Rollers 66 are rotatably mounted at certain ends of the beams of the scissors 61-64 for movement in the tracks 55 (top rollers) or the tracks 18c (bottom rollers). Top ends of the beams of the scissors 61-64 without rollers are pivotably secured to the drill floor boxes 52 and 54 at pivot points 59 and bottom ends of the beams of the scissors 61-64 without rollers are pivotably secured to the base box 18 at pivot points 18p.

The substructure 16 is raised and lowered by hydraulic cylinder apparatuses 70 (one, two, three, four or more at each end; eight shown, two pairs at each corner) which are connected at their tops to lugs 58 on the drill floor boxes 52, 54 and at their bottoms to connections 48 of the bearing pads 40.

FIGS. 2A-2G illustrate a method according to the present invention for raising a drilling rig according to the present invention from a transport position to a drilling position.

Figure 2A:
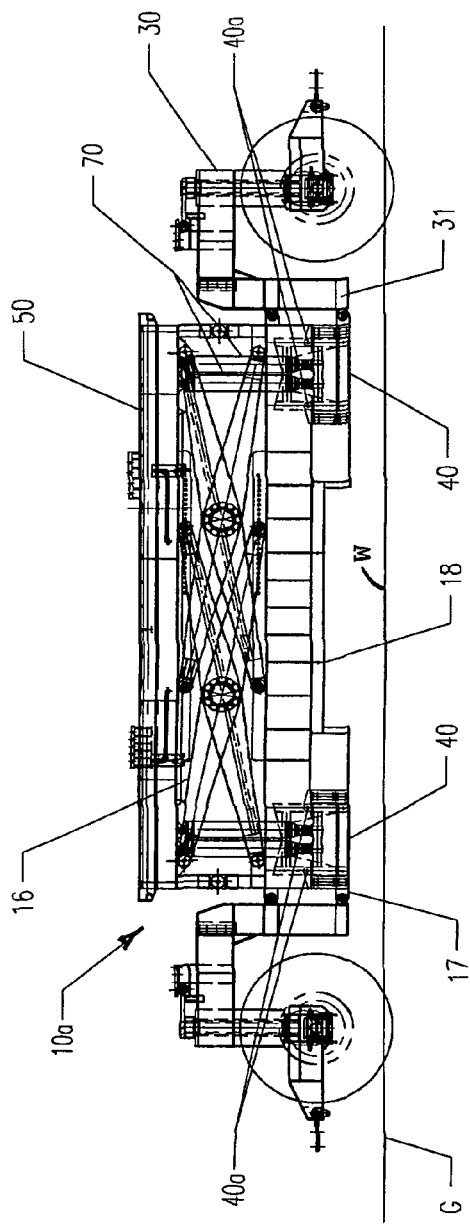
FIG. 2A is a side view of a part of the drilling rig of FIG. 1A showing a step in a method according to the present invention.

As shown in FIG. 2A, the system 10a, like the system 10 described above and like numerals indicate like parts, has been moved on its wheel assemblies 30 from an original location to the new location shown in FIG. 2A (e.g. towed by a truck or trucks with tow bars attached to the tow bar linkages 42). The substructure 16 (system 10a shown partially; may include some or all of the structures and apparatuses shown in FIGS. 1A, 1C and/or 1D) is located over a proposed well site W. As shown, the substructure 16 has not yet been raised.

Figure 2B:
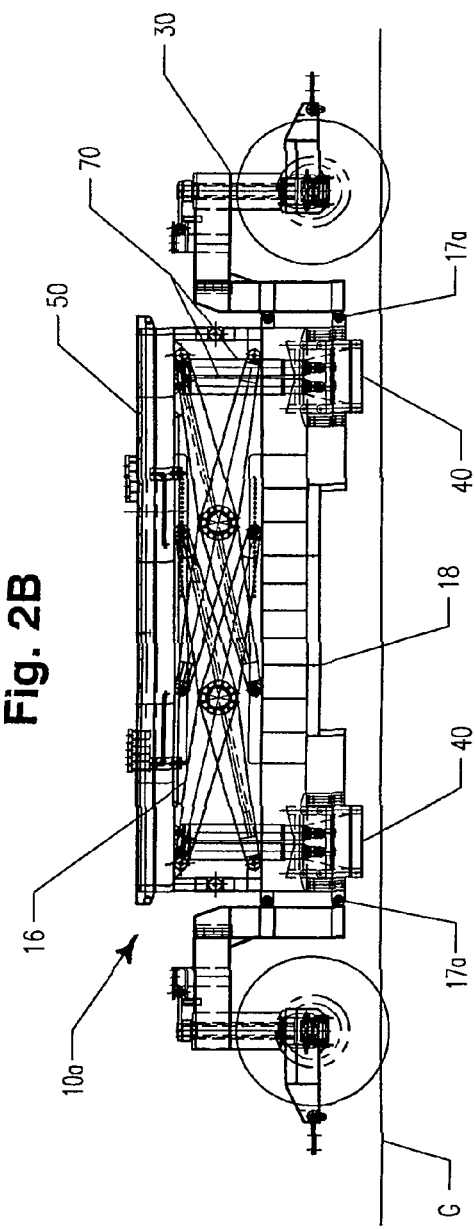
FIG. 2B is a side view of the drilling rig of FIG. 1A showing a step after the step shown in FIG. 2A.

As shown in FIG. 2B, following removal of the pins 40a, the bearing pads 40 are lowered using the hydraulic cylinders 70. As shown in FIG. 2C the hydraulic cylinders 70 are extended to lift the substructure 16, supported on the bearing pads 40 on the ground G. The pins 17a are then removed to permit disconnecting the lugs 31 from the lugs 17 to free the wheel assemblies 30 for pivoting.

As shown in FIG. 2D, the substructure 16 (and whatever, not shown, is on the substructure 16) is lowered using the hydraulic cylinders 70. The wheel assemblies pivot at wheel pivots 19. As shown in FIG. 2E, the substructure 16 is lowered until it rests on the ground G (or rig mats if they are used), with the wheel assemblies pivoted sufficiently to permit the substructure 16 to rest on the ground G. At this point, if the mast is not already mounted on the drill floor boxes 52, 54, the mast may be placed in a horizontal position on the drill floor and raised to a vertical position. (i.e., the mast can be moved as a separate load). Pins 15a which selectively secure the drill floor 50 and the base box 18 are removed so that the substructure 16 can be raised.

As shown in FIG. 2F, the substructure 16 and the drillfloor 50 (and whatever is on the drillfloor 50) are raised using the cylinders 70. The scissors apparatuses 60 are moving with their rollers in tracks from the collapsed positions of FIG. 2E to the contracting positions of FIG. 2F.

Figure 2G:
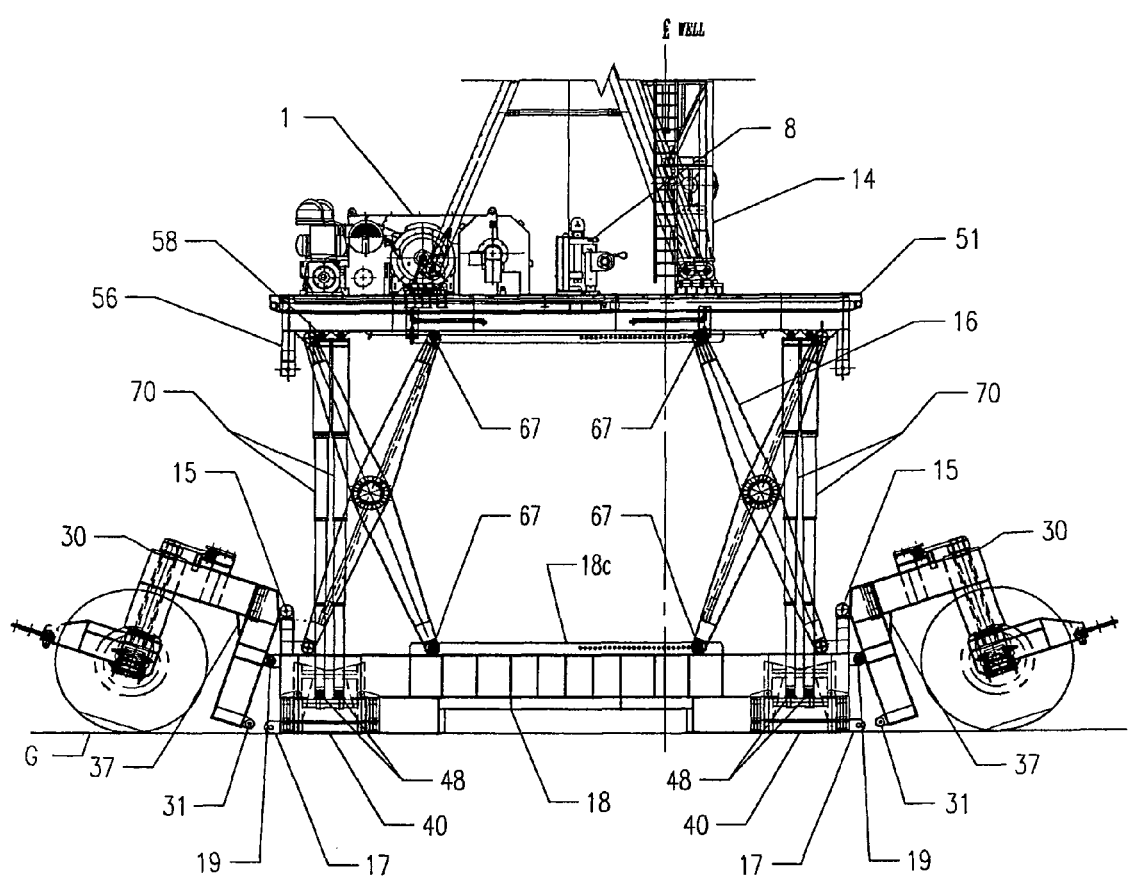
FIG. 2G is a side view showing the drilling floor of the drilling rig of FIG. 1A raised according to the present invention.
Figure 4A:
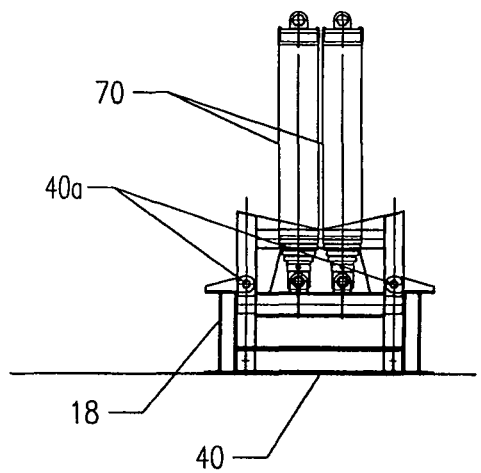
FIG. 4A is a front view of part of the rig of FIG. 1A.
Figure 4B:
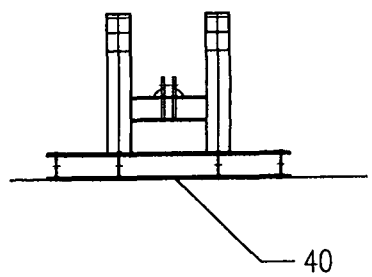
FIG. 4B is a front view of a bearing pad of the rig of FIG. 1A.
Figure 4C:
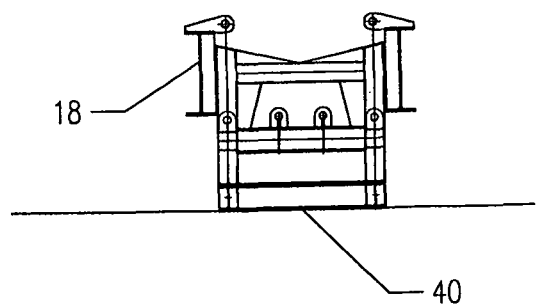
FIG. 4C is a front view of the bearing pad of FIG. 4B.

FIG. 2G illustrates the substructure 16 raised to a desired height. The top roller ends of the beams of the scissors 61-64 are pinned with pins 67 to the drill floor boxes 52, 54 and the base box 18 with pins 67 (e.g. hydraulic pins may be used).

It is within the scope of the present invention for the scissors apparatuses 60 to be folded up with the drillfloor pinned to the base box in the moving mode. Optionally the BOP stack or stacks can be removed for transport (e.g. at a 5 mph speed) using a known skidding-type BOP handling system or traditional BOP hoists to remove the stacks. At a 2.5 mph speed the BOP stack(s) may, optionally, stay onboard the rig in such a position to complement the tire loading at the four corners. The cylinders used to lift up the substructure may be the same cylinders used to raise the substructure base.

In one aspect four pairs of cylinders 70 are multistage power cylinder apparatus used with two cylinders located under each of four rig corners to raise the drillfloor and mast (if present) as one unit. The cylinders, optionally, are failsafe in that the safety factor of the hydraulics and cylinders is such that if one cylinder loses pressure, the system can still safely run with another cylinder holding the load in the same corner. If both cylinders in one corner lose pressure, then the structure, in one aspect, may still be safely lowered to the base box because the hydraulics and the cylinders have enough support ability built into them to prevent a catastrophic failure.

In one aspect the scissors apparatuses 60 are additional lifting apparatus for the BOP stacks in a cellar CR. The cellar CR can also, optionally, have spreaders with rails built in for the stack handler to roll onto from the truck bed.

The scissors apparatuses 60 are pinned at a drilling height (e.g. as in FIG. 2G) using hydraulic latch pins 67 which secure the scissor apparatuses to the guide tracks 18c and 55. In one drilling position, the rig is typically raised to a maximum height, but, in one aspect, the inherent design of the scissors apparatuses 60 allow this substructure to operate over a much larger range of heights, e.g. from 28-29 feet to 36-37 feet, although a larger design according to the present invention can provide a maximum height to over 40 feet. For example, a smaller design of the scissors apparatuses 60 may be used to create a range of 15 feet to 25 feet for an operating height.

In certain aspects, for any sized rig according to the present invention, a mast can have its top section lay down to clear the power lines. This rig may include a top drive and torque track in place. Depending on the size of the rig selected, the transport height can be much lower for a smaller rig. For example, in one aspect, a shorter portable drilling rig provided according to the present invention still has a complete drilling module. The mast may also be removed completely and shipped separately in order for the system 10a to achieve an even smaller minimum road height.

The scissors apparatuses 60 may be used in conjunction with any other sized drillfloor, large or small, tall or short, and other sized mast, in order to achieve a minimum road height and to help with clearance and stability for all families of scissor-type substructure drilling rigs. In cases where the BOP stack or other wellhead equipment is left on the well when the drilling rig (e.g. a rig 10) is ready for transport, the rig can be towed clear of the stack and then lowered to the transport height.

Systems according to the present invention, in certain aspects, aid in keeping the center of gravity of a rig in a horizontal plane at the same location in both drilling and transport modes (e.g. see FIGS. 1D and 1B; FIGS. 2G and 2A). This allows for quicker and easier rig moves with less down time for the operator, and a more evenly loaded and compact moving system design. The system, in certain aspects, also incorporates a relatively shorter wheelbase providing a more maneuverable drilling rig with a tighter turning radius, allowing for much easier transportation and location on well sites than certain current designs allow.

The present invention, therefore, provides in some, but not in necessarily all, embodiments a mobile drilling rig including: a base box, a plurality of wheel assemblies pivotably connected to the base box, each of the plurality of wheel assemblies selectively pivotable from a first position to a second position, the first position for moving the mobile drilling rig from a first location to a second location. Such a system may include one or some, in any possible combination, of the following: a substructure connected to the base box; the substructure raisable above the base box; a raising system connected to the substructure and to the base box for raising the substructure above the base box; the raising system includes a plurality of powered cylinder apparatuses for raising and lowering the substructure; wherein the raising system includes a plurality of scissors apparatuses for bracing the substructure, the scissors apparatuses each with top ends connected to the substructure and bottom ends connected to the base box; the scissors apparatuses positionable in a collapsed configuration with the substructure lowered and in an extended configuration with the substructure raised; and the scissors apparatuses releasably securable in the collapsed configuration and in the extended configuration; wherein the plurality of scissors apparatuses includes four spaced-apart scissors apparatuses, each with two centrally connected scissors members; wherein the substructure has top roller tracks; the base box has bottom roller tracks; and each scissors apparatus has a first scissors member with a top roller movable in a top roller track and a second scissors member with a bottom roller movable in a bottom roller track; a plurality of bearing pads connected to the base box, each bearing pad of the plurality of bearing pads selectively movable down from the base box to contact ground therebeneath; the bearing pads movable by the powered cylinder apparatuses; each wheel assembly including a steering apparatus for steering the wheel assembly; a drill floor on the substructure; a mast on the drill floor; wherein the mast is selectively erectable with respect to the drill floor; wherein the mobile drilling rig has four corners; and the plurality of powered cylinder apparatuses includes four pairs of two powered cylinder apparatuses each; a pair of powered cylinder apparatuses at each corner of the rig; wherein a substructure is connected to the base box, the substructure raisable above the base box and wherein one powered cylinder apparatus alone of each pair can be used to raise and lower the substructure; and/or wherein the mobile drilling rig has a center of gravity maintainable in a horizontal plane during drilling and during rig movement.

The present invention, therefore, provides in some, but not in necessarily all, embodiments a mobile drilling rig including a base box, a plurality of wheel assemblies pivotably connected to the base box, each of the plurality of wheel assemblies selectively pivotable from a first position to a second position, the first position for moving the mobile drilling rig from a first location to a second location, a substructure connected to the base box, the substructure raisable above the base box, a raising system connected to the substructure and to the base box for raising the substructure above the base box, the raising system includes a plurality of powered cylinder apparatuses for raising and lowering the substructure, and a plurality of scissors apparatuses for bracing the substructure, the scissors apparatuses each with top ends connected to the substructure and bottom ends connected to the base box, the scissors apparatuses positionable in a collapsed configuration with the substructure lowered and in an extended configuration with the substructure raised, the scissors apparatuses releasably securable in the collapsed configuration and in the extended configuration, the plurality of scissors apparatuses including four spaced-apart scissors apparatuses, each with two centrally connected scissors members, a plurality of bearing pads connected to the base box, each bearing pad of the plurality of bearing pads selectively movable down from the base box to contact ground therebeneath, the bearing pads movable by the powered cylinder apparatuses, each wheel assembly movably connected to the base box and including a steering apparatus for steering the wheel assembly, a drill floor on the substructure, a mast on the drill floor, and wherein the mast is selectively erectable with respect to the drill floor.

The present invention provides, therefore, in at least certain, but not necessarily all, embodiments a mobile drilling rig with a base box, a substructure connected to the base box, the substructure raisable above the base box, a raising system connected to the substructure and to the base box for raising the substructure above the base box, the raising system includes a plurality of powered cylinder apparatuses for raising and lowering the substructure, the raising system includes a plurality of scissors apparatuses for bracing the substructure, the scissors apparatuses each with top ends connected to the substructure and bottom ends connected to the base box, the scissors apparatuses positionable in a collapsed configuration with the substructure lowered and in an extended configuration with the substructure raised, and the scissors apparatuses releasably securable in the collapsed configuration and in the extended configuration. Such a rig may have one or some, in any possible combination, of the following: wherein the plurality of scissors apparatuses includes four spaced-apart scissors apparatuses, each with two centrally connected scissors members; wherein the substructure has top roller tracks, the base box has bottom roller tracks, and each scissors apparatus has a first scissors member with a top roller movable in a top roller track and a second scissors member with a bottom roller movable in a bottom roller track; a drill floor on the substructure, a mast on the drill floor, and wherein the mast is selectively erectable with respect to the drill floor.

The present invention, therefore, provides in some, but not in necessarily all, embodiments a method for moving a mobile drilling rig, the method including: pivoting wheel assemblies pivotably connected to a base box of a rig from a drilling position to a movement position, the rig comprising a base box, a plurality of wheel assemblies pivotably connected to the base box, each of the plurality of wheel assemblies selectively pivotable from a first position to a second position, the first position for moving the mobile drilling rig from a first location to a second location; securing the wheel assemblies in the movement position, and moving the mobile drilling rig on the wheel assemblies. Such a method may include one or some, in any possible combination, of the following: a substructure connected to the base box, the substructure raisable above the base box, a raising system connected to the substructure and to the base box for raising the substructure above the base box, the method including raising with the raising system the substructure above the base box; wherein the raising system includes a plurality of powered cylinder apparatuses for raising and lowering the substructure; wherein the raising system includes a plurality of scissors apparatuses for bracing the substructure, the scissors apparatuses each with top ends connected to the substructure and bottom ends connected to the base box, the scissors apparatuses positionable in a collapsed configuration with the substructure lowered and in an extended configuration with the substructure raised, and the scissors apparatuses releasably securable in the collapsed configuration and in the extended configuration, the method including moving the scissors apparatuses from the collapsed configuration to the extended configuration as the substructure is raised; wherein the substructure has top roller tracks, the base box has bottom roller tracks, and each scissors apparatus has a first scissors member with a top roller movable in a top roller track and a second scissors member with a bottom roller movable in a bottom roller track, the method including moving the top rollers in the top roller tracks, and moving the bottom rollers in the bottom roller tracks; wherein a plurality of bearing pads are connected to the base box, each bearing pad of the plurality of bearing pads selectively movable with respect to the base box, the bearing pads in contact with ground during drilling and movable by the powered cylinder apparatuses, the method including raising the bearing pads above the ground to facilitate movement of the mobile drilling rig; wherein each wheel assembly including a steering apparatus for steering the wheel assembly, the method including steering each wheel assembly with its corresponding steering apparatus; wherein there is a drill floor on the substructure, a mast on the drill floor, and wherein the mast is selectively erectable and lowerable with respect to the drill floor, the method including lowering the mast to facilitate movement of the mobile drilling rig; wherein the raising system includes a plurality of powered cylinder apparatuses for raising and lowering the substructure, the mobile drilling rig has four corners, and the plurality of powered cylinder apparatuses includes four pairs of two powered cylinder apparatuses each, a pair of powered cylinder apparatuses at each corner of the rig, and wherein a substructure is connected to the base box, the substructure raisable above the base box and wherein one powered cylinder apparatus alone of each pair can be used to raise and lower the substructure, the method including operating only one powered cylinder apparatus of one pair of powered cylinder apparatuses during raising or lowering of the substructure; and/or wherein the mobile drilling rig has a center of gravity maintainable in a horizontal plane during drilling and during rig movement, the method including maintaining the center of gravity of the mobile drilling rig in a horizontal plane during drilling and during rig movement.

In conclusion, therefore, it is seen that the present invention and the embodiments disclosed herein and those covered by the appended claims are well adapted to carry out the objectives and obtain the ends set forth. Certain changes can be made in the subject matter without departing from the spirit and the scope of this invention. It is realized that changes are possible within the scope of this invention and it is further intended that each element or step recited in any of the following claims is to be understood as referring to the step literally and/or to all equivalent elements or steps. The following claims are intended to cover the invention as broadly as legally possible in whatever form it may be utilized. The invention claimed herein is new and novel in accordance with 35 U.S.C. §102 and satisfies the conditions for patentability in §102. The invention claimed herein is not obvious in accordance with 35 U.S.C. §103 and satisfies the conditions for patentability in §103. This specification and the claims that follow are in accordance with all of the requirements of 35 U.S.C. §112. The inventor may rely on the Doctrine of Equivalents to determine and assess the scope of the invention and of the claims that follow as they may pertain to apparatus not materially departing from, but outside of, the literal scope of the invention as set forth in the following claims. All patents and applications identified herein are incorporated fully herein for all purposes. It is the express intention of the applicant not to invoke 35 U.S.C. §112, paragraph 6 for any limitations of any of the claims herein, except for those in which the claim expressly uses the words 'means for' together with an associated function. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

What is claimed is:

1. A mobile drilling rig comprising
  a base box,
  a plurality of wheel assemblies adapted to facilitate movement of the mobile drilling rig from a first rig location, wherein each of the plurality of wheel assemblies is pivotably connected to the base box and is adapted to be selectively pivotable from a moving mode position during said movement to a drilling mode position during drilling operations,
  a substructure connected to the base box, and
  a raising system operatively coupled to the substructure and to the base box, wherein the raising system is adapted to raise the substructure above the base box to a raised drilling position, to support the substructure in said raised drilling position during drilling operations, and to substantially maintain the substructure in said raised drilling position during said movement of the mobile drilling rig.

2. The mobile drilling rig of claim 1 wherein the raising system comprises a plurality of powered cylinder apparatuses that are adapted for raising and lowering the substructure.

3. The mobile drilling rig of claim 1 wherein the raising system comprises a plurality of scissors apparatuses that are adapted for bracing the substructure, each of the scissors apparatuses comprises top ends that are connected to the substructure and bottom ends that are connected to the base box, and each of the scissors apparatuses is adapted to be positionable and releasably secured in a collapsed configuration with the substructure lowered and in an extended configuration with the substructure raised.

4. The mobile drilling rig of claim 3 wherein the plurality of scissors apparatuses comprises four spaced-apart scissors apparatuses, each of the four spaced-apart scissors apparatuses comprising two centrally connected scissors members.

5. The mobile drilling rig of claim 4 wherein the substructure comprises top roller tracks, the base box comprises bottom roller tracks, and each of the plurality of scissors apparatuses comprises a first scissors member comprising a top roller that is adapted to be movable in a top roller track and a second scissors member comprising a bottom roller that is adapted to be movable in a bottom roller track.

6. The mobile drilling rig of claim 2 further comprising a plurality of bearing pads connected to the base box, wherein each of the plurality of bearing pads is adapted to be selectively movable by a respective one of the powered cylinder apparatuses down from the base box to contact ground therebeneath.

7. The mobile drilling rig of claim 1 wherein each of the plurality of wheel assemblies comprises a steering apparatus that is adapted for steering a respective one said wheel assemblies.

8. The mobile drilling rig of claim 1 further comprising a drill floor on the substructure.

9. The mobile drilling rig of claim 8 further comprising a mast on the drill floor.

10. The mobile drilling rig of claim 9 wherein the mast is adapted to be selectively erectable with respect to the drill floor.

11. The mobile drilling rig of claim 2 wherein the mobile drilling rig has four corners, and the plurality of powered cylinder apparatuses comprises a pair of powered cylinder apparatuses positioned proximate each of said four corners.

12. The mobile drilling rig of claim 11 wherein each pair of powered cylinder apparatuses are configured so that one powered cylinder apparatus from each pair can be used to raise and lower the substructure.

13. The mobile drilling rig of claim 1 wherein the mobile drilling rig is adapted to maintain a center of gravity in a horizontal plane during drilling operations and during rig movement.

14. A mobile drilling rig comprising
  a base box,
  a plurality of wheel assemblies adapted to facilitate movement of the mobile drilling rig from a drilling rig location, wherein each of the plurality of wheel assemblies is pivotably connected to the base box and is adapted to be selectively pivotable from a moving mode position during said movement to a drilling mode position during drilling operations, and wherein each of the plurality of wheel assemblies comprises a steering apparatus that is adapted for steering a respective one said wheel assemblies,
  a substructure connected to the base box,
  a raising system operatively coupled to the substructure and to the base box that is adapted to raise the substructure above the base box to a raised drilling position, to support the substructure in said raised drilling position during drilling operations, and to substantially maintain the substructure in said raised drilling position during said movement of the mobile drilling rig, wherein the raising system comprises a plurality of powered cylinder apparatuses that are adapted for raising and lowering the substructure and four spaced-apart scissors apparatuses that are adapted for bracing the substructure, wherein each of the scissors apparatuses comprises two centrally connected scissors members, top ends that are connected to the substructure and bottom ends that are connected to the base box, and wherein each of the scissors apparatuses is adapted to be positionable and releasably securable in a collapsed configuration with the substructure lowered and in an extended configuration with the substructure raised, a plurality of bearing pads connected to the base box, wherein each of the plurality of bearing pads is adapted to be selectively movable by a respective one of the powered cylinder apparatuses down from the base box to contact ground therebeneath, a drill floor on the substructure, and a mast on the drill floor, wherein the mast is adapted to be selectively erectable with respect to the drill floor.

15. A mobile drilling rig comprising a base box, a substructure connected to the base box, a raising system operatively coupled to the substructure and to the base box that is adapted for raising the substructure above the base box to a raised drilling position, to support the substructure in said raised drilling position during drilling operations, and to substantially maintain the substructure in said raised drilling position during movement of the mobile drilling rig from a drilling rig location, wherein the raising system comprises a plurality of powered cylinder apparatuses that are adapted for raising and lowering the substructure and a plurality of scissors apparatuses that are adapted for bracing the substructure, wherein each of the scissors apparatuses comprises top ends that are connected to the substructure and bottom ends that are connected to the base box, and wherein each of the scissors apparatuses is adapted to be positionable and releasably securable in a collapsed configuration with the substructure lowered and in an extended configuration with the substructure raised.

16. The mobile drilling rig of claim 15 wherein the plurality of scissors apparatuses comprises four spaced-apart scissors apparatuses, each of the four spaced-apart scissors apparatuses comprising two centrally connected scissors members.

17. The mobile drilling rig of claim 15 wherein the substructure comprises top roller tracks, the base box comprises bottom roller tracks, and each of the plurality of scissors apparatuses comprises a first scissors member comprising a top roller that is adapted to be movable in a top roller track and a second scissors member comprising a bottom roller that is adapted to be movable in a bottom roller track.

18. The mobile drilling rig of claim 15 further comprising a drill floor on the substructure and a mast on the drill floor, wherein the mast is adapted to be selectively erectable with respect to the drill floor.

19. The mobile drilling rig of claim 15, wherein an open space is defined within the substructure and below the drill floor when the substructure is raised to said drilling position by said raising system, a size of said open space being adapted to facilitate said movement of the mobile drilling rig over pressure-retaining equipment that is mounted on a wellhead at said first rig location while the substructure is maintained in said raised drilling position.

20. The mobile drilling rig of claim 19, wherein a size of said open space is adapted to facilitate said movement of the mobile drilling rig over a BOP stack mounted on said wellhead and positioned in said open space.

21. A method, comprising:

raising a substructure of the mobile drilling rig relative to a base box of the mobile drilling rig to a raised drilling position so as to define an open space within the substructure and below a drill floor positioned on the substructure, a size of said open space being adapted to facilitate movement of the mobile drilling rig over pressure-retaining equipment that is mounted on a wellhead at a drilling rig location while maintaining the substructure in said raised drilling position, wherein raising the substructure comprises actuating a raising system operatively coupled to the substructure and the base box;

pivoting each of a plurality of wheel assemblies operatively coupled to the base box from a drilling mode configuration to a moving mode configuration;

releasably securing each of the plurality of wheel assemblies in the moving mode configuration, and moving the mobile drilling rig from a first rig location using said plurality of wheel assemblies secured in the moving mode configuration while substantially maintaining the substructure in said raised drilling position during said movement.

22. The method of claim 21, further comprising moving the mobile drilling rig from above a BOP stack that is positioned in said open space and mounted on a wellhead at said first rig location, actuating the raising system to lower the substructure from said raised drilling position to a lowered transport position proximate the base box, and thereafter moving the mobile drilling rig to a second rig location.

23. The method of claim 22, further comprising releasably securing the substructure to the base box.

24. The method of claim 21, wherein actuating the raising system comprises actuating at least one of a plurality of powered cylinder apparatuses operatively coupled to the substructure and the base box.

25. The method of claim 21, wherein actuating the raising system comprises actuating a plurality of scissors apparatuses operatively coupled to the substructure and the base box.

26. The method of claim 25, wherein actuating the plurality of scissors apparatuses comprises moving a top roller of each of the plurality of scissors apparatuses along a top track disposed along the substructure and moving a bottom roller of each of the plurality of scissors apparatuses along a bottom track disposed along the base box.

27. The method of claim 26, wherein actuating the plurality of scissors apparatuses comprises moving each of the plurality of scissors apparatuses between an extended configuration, wherein the substructure is in said raised drilling position, and a collapsed configuration, wherein the substructure is positioned proximate the base box.

28. The method of claim 21, further comprising steering each of the plurality of wheel assemblies using a plurality of steering apparatuses, wherein each one of the plurality of steering apparatuses is operatively coupled to a respective one of the plurality of wheel assemblies.

29. The method of claim 21, further comprising selectively raising each one of a plurality of bearing pads that are in contact with ground, wherein each of the plurality of bearing pads are operatively coupled to the base box.

30. The method of claim 21, further comprising lowering a mast of the mobile drilling rig relative to a drill floor positioned above the substructure.

31. The method of claim 21, further comprising maintaining a center of gravity of the mobile drilling rig in a substantially constant horizontal plane from drilling operations throughout movement operations.

32. The mobile drilling rig of claim 1, wherein the plurality of wheel assemblies are adapted to facilitate movement of the mobile drilling rig from said first rig location to a second rig location.

33. The mobile drilling rig of claim 32, wherein the raising apparatus is adapted to substantially maintain the substructure in said raised drilling position during said movement of the mobile drilling rig to said second rig location.

34. The mobile drilling rig of claim 32, wherein the raising apparatus is adapted to substantially maintain the substructure in said raised drilling position during a first part of said movement of the mobile drilling rig to said second rig location and to lower the substructure to a lowered transport position proximate the base box during a second part of said movement to said second rig location.

35. The mobile drilling rig of claim 1, wherein the raising apparatus is further adapted to support drilling loads while maintaining the substructure in said raised drilling position during said drilling operations.

36. The mobile drilling rig of claim 10, wherein the mast is adapted to be maintained in an erected position during said movement of the mobile drilling rig.

37. The method of claim 21, further comprising substantially maintaining the substructure in said raised drilling position while moving the mobile drilling rig from said first rig location to a second rig location.

38. The method of claim 21, further comprising raising, to an erected position, a mast of the mobile drilling rig relative to a drill floor positioned above the substructure, and maintaining the mast in said erected position during said movement of the mobile drilling rig.

39. The method of claim 21, further comprising performing drilling operations with the mobile drilling rig, wherein performing said drilling operations comprises using the raising system to maintain the substructure in said raised drilling position and to support drilling loads during said drilling operations.

40. The mobile drilling rig of claim 8, wherein an open space is defined within the substructure and below the drill floor when the substructure is raised to said drilling position by said raising system, a size of said open space being adapted to facilitate said movement of the mobile drilling rig over pressure-retaining equipment that is mounted on a wellhead at said first rig location while the substructure is maintained in said raised drilling position.

41. The mobile drilling rig of claim 40, wherein a size of said open space is adapted to facilitate said movement of the mobile drilling rig over a BOP stack mounted on said wellhead and positioned in said open space.

42. The method of claim 22, wherein moving the mobile drilling rig from above the BOP stack comprises moving the mobile drilling rig so that the BOP stack passes through said open space within the substructure and below the drill floor.

43. The mobile drilling rig of claim 41, wherein the raising apparatus is adapted to substantially maintain the substructure in said raised drilling position until the mobile drilling rig is moved clear of said BOP stack and to thereafter lower the substructure to a lowered transport position proximate the base box for transport to a second rig location.

\* \* \* \* \*